United States Patent [19]

McKenzie

[11] Patent Number: 5,489,512
[45] Date of Patent: Feb. 6, 1996

[54] METHOD OF OPTIMIZING A NUCLEIC ACID HYBRIDIZATION ASSAY FOR DETECTION OF SALMONELLA IN RV GROWTH MEDIA

[75] Inventor: R. Scott McKenzie, Warwick, R.I.

[73] Assignee: Amoco Corporation

[21] Appl. No.: 131,021

[22] Filed: Oct. 4, 1993

Related U.S. Application Data

[63] Continuation of Ser. No. 793,018, Nov. 15, 1991, abandoned.

[51] Int. Cl.$^6$ .................................................. C12Q 1/68
[52] U.S. Cl. ........................................ 435/6; 935/78
[58] Field of Search ................................. 435/6; 935/78

[56] References Cited

U.S. PATENT DOCUMENTS 4,689,295  8/1987  Taber et al. ................................. 435/6

FOREIGN PATENT DOCUMENTS 0338591  10/1989  European Pat. Off. .................. 435/6

OTHER PUBLICATIONS

Peterz, M. et al. (1989) Journal of Applied Bacteriology vol. 66, pp. 523–528.
Nucleic Acid Hybridization: A Practical Guide, B. D. Hames & S. J. Higgins, eds., 1985, IRL Press, Oxford, pp. 6–7.

Primary Examiner—Margaret Parr
Assistant Examiner—Lisa Arthur
Attorney, Agent, or Firm—Norval B. Galloway

[57] ABSTRACT

A method for enhancing the hybridization signal of a nucleic acid hybridization assay for the DNA or RNA of a Salmonella in a sample by adding the sample to a RV growth medium under conditions sufficient to allow any Salmonella in the sample to propagate, propagating Salmonella, if any, in the medium for a time sufficient to allow the number of Salmonella to reach a predetermined titer, removing trace minerals from the medium, adding a nucleic acid probe to the medium under stringency conditions sufficient to allow the probe to preferentially hybridize with the Salmonella, if any, to form hybridization products that emit an enhanced signal, and assaying the medium to detect the enhanced signal. The method is especially suited for detecting Salmonella in food samples.

10 Claims, 4 Drawing Sheets

EVALUATION OF THE COLORIMETRIC GENE TRAK ASSAY FOR SALMONELLA INCORPORATING AN ALTERNATIVE EUROPEAN ENRICHMENT PROTOCOL-SUMMARY

RESULTS

| SAMPLE | ORGANISM | INOCULUM (cells\25g) | GENE TRAK USA | GENE TRAK EUROPEAN MK | GENE TRAK EUROPEAN RV+NaCitrate | CONVENTIONAL USA | CONVENTIONAL EUROPEAN | NOTES |
|---|---|---|---|---|---|---|---|---|
| SAVOURY CHEESE SNACKS | CONTROL | 0 | -(x2) | -(x2) | -(x2) | -(x2) +* | -(x2) - | *GNB-ve |
| | S.MANCHESTER CRA 817 | 24<br>20 | +<br>+ | +<br>+ | +<br>+ | +<br>+ | +<br>+ | |
| | CRA 818 | 78<br>22<br>11 | +<br>+<br>+ | +<br>+<br>-* | +<br>+<br>+ | +<br>+<br>+ | +<br>+<br>+ | *GNB+ve |
| CHICKEN | CONTROL | 0 | -(x3) | -(x3) | -(x3) | -(x3) | -(x3) | |
| | S.HADAR CRA 831 | 142<br>21<br>21 | +<br>+<br>+ | +<br>+<br>+ | +<br>+<br>+ | +<br>+<br>+ | +<br>+<br>+ | |
| | S.HEIDELBERG CRA 832 | 34<br>26 | +<br>+ | +<br>+ | +<br>+ | +<br>+ | +<br>+ | |
| | S.INDIANA CRA 71 | 20 | + | + | + | -* | -* | *ATYPICAL BIOCHEMISTRY |
| POWDERED BABY MILK | CONTROL | 0 | -(x3) | -(x3) | -(x3) | -(x3) | -(x3) | |
| | S.EALING CRA 511 | 30<br>15 | +<br>+ | +<br>+ | +<br>+ | +<br>+ | +<br>+ | |
| | S.INFANTIS CRA 816 | 13<br>20 | +<br>+ | +<br>+ | +<br>+ | +<br>+ | +<br>+ | |

EVALUATION OF THE COLORIMETRIC GENE TRAK ASSAY FOR SALMONELLA INCORPORATING AN ALTERNATIVE EUROPEAN ENRICHMENT PROTOCOL-SUMMARY

| SAMPLE | ORGANISM | INOCULUM (cells\25g) | RESULTS | | | | | NOTES |
|---|---|---|---|---|---|---|---|---|
| | | | GENE TRAK | | | CONVENTIONAL | | |
| | | | USA | EUROPEAN MK | EUROPEAN RV+NaCitrate | USA | EUROPEAN | |
| MINCED BEEF | CONTROL | 0 | -(x12) -,* | -(x12) -,* | -(x12) + | -(x12) - | -(x12) + | *GNB-ve |
| | S.NEWPORT CRA 77 | 32 18 19 | + + + | + + + | + + + | + + + | + + + | |
| | S.AGONA S118405\90 | 47 24 | + + | + + | + + | + + | + + | |
| | S117130\90 | 26 26 | + + | + + | + + | + + | + + | |
| POWDERED LOW FAT MILK | CONTROL | 0 | -(x2) - | -(x2) - | -(x2) - | -(x2) - | -(x2) +,* | *+ve from MK broth (GNB-ve) |
| | S.VIRCHOW CRA 670 | 9 3 | + + | + + | + + | + + | + + | |
| | S.TYPHIMURIUM CRA 834 | 26 21 | + + | - + | -,* + | + + | - + | *GNB-ve |
| CHOCOLATE | CONTROL | 0 | -(x2) | -(x2) | -(x2) | -(x2) | -(x2) | |
| | S.NAPOLI CRA 76 | 39 43 | + + | + + | + + | + + | + + | |
| | S.TEL-EL-KEBIR 9696\1 | 57 | + | + | + | + | + | |
| | S.IBADAN 9696\2 | 32 | + | + | + | + | + | |

EVALUATION OF THE COLORIMETRIC GENE TRAK ASSAY FOR SALMONELLA INCORPORATING AN ALTERNATIVE EUROPEAN ENRICHMENT PROTOCOL-SUMMARY

| | | | RESULTS | | | | |
|---|---|---|---|---|---|---|---|
| SAMPLE | ORGANISM | INOCULUM (cells\25g) | GENE TRAK USA | GENE TRAK EUROPEAN MK | GENE TRAK EUROPEAN RV+NaCitrate | CONVENTIONAL USA | CONVENTIONAL EUROPEAN | NOTES |
| FRESH EGG | CONTROL | 0 | -(x4) | -(x4) | -(x4) | -(x4) | -(x4) | |
| | S.ENTERITIDIS CRA 786 | 28 / 77 | + + | + + | + + | + + | + + | |
| | CRA 787 | 18 / 53 | + + | + + | + + | + + | + + | |
| | CRA 788 | 11 / 0 | + + | + + | + + | + + | + + | |
| | CRA 789 | 40 / 38 | + + | + + | + + | + + | + + | |
| | CRA 790 | 43 / 17 | + + | + + | + + | + + | + + | |
| POWDERED EGG | CONTROL | 0 | -(x3) | -(x3) | -(x3) | -(x3) | -(x3) | |
| | S.ENTERITIDIS CRA 786 | 90 / 23 | + + | + + | + + | + + | + + | |
| | S.ARIZONA CRA 833 | 24 / 29 | + + | + + | + + | + + | +/-* | *weak serology |
| ANIMAL FEED (suspected natural contamination) | MIXER MEAT+BONE | 0 / 0 | - - | - - | - - | - - | - - | |

FIG. 1C

EVALUATION OF THE COLORIMETRIC GENE TRAK ASSAY FOR SALMONELLA INCORPORATING AN ALTERNATIVE EUROPEAN ENRICHMENT PROTOCOL-SUMMARY

| SAMPLE | ORGANISM | INOCULUM (cells\25g) | RESULTS | | | | | NOTES |
|---|---|---|---|---|---|---|---|---|
| | | | GENE TRAK USA | GENE TRAK EUROPEAN MK | GENE TRAK EUROPEAN RV+NaCitrate | CONVENTIONAL USA | CONVENTIONAL EUROPEAN | |
| BEAN SPROUTS | CONTROL | 0 | -(x2) - | -(x2) - | -(x2) + | -(x2) - | -(x2) + | |
| | S.SAINT-PAUL S103126\88 | 29 | -* | + | + | - | + | *GNB-ve |
| | | 29 | - | - | - | - | - | All GNB-ve |
| | | 75 | -* | + | + | - | + | *GNB-ve |
| | | 199 | +* | + | + | + | + | *Low +ve value |
| POWDERED BABY MILK | S.TYPHIMURIUM (from BCR capsules) | CONTROL | - | - | - | - | - | |
| | | ~5 | + | + | + | + | + | |
| | | ~5 | + | + | + | + | + | |
| POWDERED LOW FAT MILK | S.TYPHIMURIUM (from BCR capsules) | CONTROL | -(x2) + | -(x2) - | -(x2) - | -(x2) + | -(x2) - | |
| | | ~5 | + | - | - | + | + | *GNB+ve |
| | | ~5 | + | -* | -* | + | - | |
| | | ~5 | + | -* | + | + | + | *GNB+ve |

FIG. 1D

METHOD OF OPTIMIZING A NUCLEIC ACID HYBRIDIZATION ASSAY FOR DETECTION OF SALMONELLA IN RV GROWTH MEDIA

This is a continuation of application Ser. No. 07/793,018 filed on Nov. 15, 1991, now abandoned.

BACKGROUND OF THE INVENTION

This invention relates to assay methods for detecting undesired microorganisms, e.g., Salmonella, in samples, e.g., of food products.

It has long been known that it is beneficial to test for microorganisms to assess the safety and quality of raw materials and finished products, the hygiene within production environments, the efficacy of physical and chemical preservation processes, the microbiological stability of finished products (shelf-life testing), and to meet safety and quality specifications.

However, conventional tests for microorganisms are typically labor intensive and material expensive, often have low precision and accuracy, and need long incubation periods. Results for conventional test are often obtained only after the raw materials have been used, perishable products have been distributed, or short shelf-life products have been consumed. Consequently, it is important to perform such tests as rapidly, accurately, precisely, and economically as possible.

One major concern relating to food products is Salmonella contamination. The genus Salmonella includes many serovars that cause enteric disease in man. The ingestion of salmonella-contaminated food can cause food poisoning that may be fatal. Standard tests for Salmonella can take more than a week to demonstrate that a sample is free from contamination. Another problem with conventional tests is that Salmonella serotypes are a large physiologically diverse group that require a range of media to be used for their detection. Typical conventional tests to detect Salmonella in food include resuscitation or preenrichment in liquid media, enrichment, i.e., selective culture, in liquid media, isolation of individual colonies on selective and differential agars, and confirmation of identity using biochemistry and serology techniques.

Recently, nucleic acid probes have been utilized to test for microorganism contamination. Such probes are designed to hybridize preferentially with the DNA or RNA of specific target organisms that may be present in a sample and are typically labelled so that they can be detected if they hybridize with the target microorganism. Samples are inoculated into liquid growth media in which the target microorganisms, if any, can propagate. Thereafter, the nucleic acid probes are added under conditions that allow preferential hybridization, and the hybridization products, if any, are detected by various assays, e.g., colorimetric assays.

Such nucleic acid probe test methods are accurate and quick, but the assays for the hybridization products can be hampered by the growth media in which the target microorganisms are propagated.

The European marketplace typically utilizes microorganism enrichment strategies different than those used in the U.S. For example, the U.S. market typically enriches according to methodology described in the Bacterial Analytical Manual (BAM), an FDA publication, e.g., using selenite cysteine and tetrathionate-Brilliant Green broths for the enrichment of Salmonella from foods. The Europeans, however, use RV medium almost exclusively for this purpose. RV medium is composed of the following ingredients per liter of water: 5.0 g soya peptone, 8.0 g NaCl, 1.6 g $KH_2PO_4$, 40.0 g $MgCl_2$, and 0.4 g Malachite Green (pH= $5.2\pm0.2$).

However, this RV medium has been shown to be detrimental to the use of DNA probe hybridization reactions. For example, if a food sample containing Salmonella is enriched according to BAM methodology, the endpoint signal, in a colorimetric assay for hybridization products is expected to be between 1.0 and 2.0 O.D. units (at 450 nm). However, when the same sample is enriched using RV medium, the endpoint signal for the same assay is between 0.0 and 0.1 O.D. units, with many samples being read as false negatives.

The inventors have developed a solution to this low signal problem for such assays, in particular, to perform in the European marketplace.

SUMMARY OF THE INVENTION

The invention is based on the discovery that hybridization assays are inhibited when certain strains of bacteria, e.g., Salmonella, are enriched and then assayed in certain media, e.g., RV medium. Studies have shown that this inhibition is eliminated when trace minerals, e.g., magnesium, are removed from the medium before the hybridization assay is performed. It is believed that in the case of RV medium, some metabolic effect of the bacteria on the medium liberates trace minerals that subsequently interfere with hybridization, but which do not interfere with hybridization as present in the fresh medium.

In general, the invention features a method for enhancing the hybridization signal of a nucleic acid hybridization assay for the DNA or RNA of a target organism, e.g., Salmonella, in a sample, e.g., food sample, by adding the sample to a growth medium under conditions sufficient to allow any target organism in the sample to propagate, propagating the organism, if any, in the medium for a time sufficient to allow the number of target organisms to reach a predetermined titer, removing trace minerals from the medium, adding a nucleic acid probe to the medium under stringency conditions sufficient to allow the probe to preferentially hybridize with the desired target organism, if any, to form hybridization products that emit an enhanced signal, and assaying the medium to detect the enhanced signal.

In preferred embodiments, the invention features removal of trace minerals, e.g., magnesium, by chelating the medium with an amount of a chelating agent, e.g., sodium citrate or ethylenediaminetetraacetic acid, sufficient to prevent interference of the hybridization signal by trace minerals in the medium, e.g., RV medium.

When sodium citrate is used as the chelating agent, it may be added to the medium to achieve a final concentration of sodium citrate in the medium of 0.05M to 0.5M, and more preferably, 0.1M to 0.2M.

The invention also features removal of trace minerals by centrifuging the medium to recover the target organism, if any, and resuspending the organism in fresh medium.

Other features and advantages of the invention will be apparent from the following detailed description thereof, and from the claims.

BRIEF DESCRIPTION OF THE DRAWINGS

FIGS. 1A, 1B, 1C, 1D. The figures show an evaluation of hybridization results when using the colorimetric Gene-Trak Assay for Salmonella as compared to other conventional Salmonella enrichment methods.

DETAILED DESCRIPTION

The Tables are first briefly described.

Tables 1A to 1D show the results of colorimetric assays for various food products and various Salmonella strains in conventional enrichment media with and without sodium citrate added just prior to hybridization.

The inventor has discovered that by removing excess trace minerals, e.g., magnesium, from the growth medium after the cells have been propagated, the hybridization reaction, normally inhibited by the presence of such trace minerals, is optimized. By not changing the enrichment medium until after the microorganisms have grown to appropriate titers, growth conditions remain optimal. Removal of the trace minerals during the enrichment stage is undesirable, because these minerals are required for proper growth of the microorganisms in the samples. This removal of the trace minerals following enrichment and just prior to nucleic acid probe hybridization allows optimal growth and precise positive sample identification.

In preferred embodiments of the invention, the trace minerals, e.g., magnesium, are removed by a chelating agent, preferably sodium citrate. Ethylenediaminetetraacetic acid (EDTA) may also be used. The chelating agent effectively prevents the trace minerals from interfering with the assay, leaving only a small amount of unchelated minerals in the sample, which does not interfere with the hybridization assays. This amount of unchelated mineral can be calculated for given concentrations of the chelating agent, the mineral to be chelated, and the chelation constant of the particular agent for that particular mineral. RV medium is one widely used example of a standard medium that has an interfering amount of such trace minerals after bacterial growth has occurred.

A less preferred, and more cumbersome method of removing the interfering trace minerals is to centrifuge the medium, and any microorganisms therein, remove the supernatant, and then to resuspend the microorganisms from the sample, if any, in a standard hybridization buffer, or in fresh medium, e.g., RV medium. It has been found that the trace minerals in fresh RV medium do not interfere with the Gene-Trak Systems (GTS) (Framingham, Mass.) hybridization assay.

Experiments

The basic concept of the invention was tested using samples of *S. enteritidis* and *S. typhimurium* in RV medium and using a standard Gene-Trak Systems (GTS) (Framingham, Mass.) colorimetric assay following the manufacturer's directions. The RV medium samples were serially diluted using 10 parts Gram-Negative (GN) medium to 1 part RV medium. GN medium is used as an optimum growth medium for gram-negative bacteria such as Salmonella.

A 3.0M sodium citrate solution was prepared to add to the medium prior to hybridization. Heat was required to get the sodium citrate into solution.

Samples containing *S. enteritidis* or *S. typhimurium* were pretreated by adding 17 parts of the 3.0M sodium citrate solution to 500 parts of the sample medium to achieve a final concentration of sodium citrate of 0.1M before hybridization was started. The pretreated samples were then incubated for 15 minutes and assayed using the GTS colorimetric assay. The table below shows O.D. values (at 450 nm) for two samples at each of the various solutions. The "spun neat" controls were centrifuged and resuspended in fresh GN medium or fresh RV medium and diluted in 10 parts GN medium.

|  | *S. enteritidis* | | *S. typhimurium* | |
| --- | --- | --- | --- | --- |
|  | Na citrate added | No Na citrate | Na citrate added | No Na citrate |
| 1/1 | 2.14, 2.10 | 0, 0 | 2.10, 2.04 | 2.04, 2.10 |
| 1/5 | 1.95, 1.80 | 0, 0 | 2.00, 2.07 | 1.61, 1.71 |
| 1/25 | 1.51, 1.52 | 0.33, 0.20 | 1.74, 1.65 | 1.21, 1.04 |
| 1/50 | 1.21, 1.33 | 0.57, 0.46 | 1.51, 1.48 | 1.00, 1.06 |
| 1/100 | 0.71, 0.82 | 0.62, 0.59 | 1.21, 1.17 | 1.05, 0.95 |
| 1/250 | 0.34, 0.43 | 0.34, 0.34 | 0.74, 0.80 | 0.64, 0.61 |
| 1/500 | 0.21, 0.24 | 0.21, 0.20 | 0.34, 0.35 | 0.42, 0.35 |
| Spun Neat in GN | 2.01 | 1.95 | 2.12 | 2.02 |
| Spun Neat in RV/GN | 2.03 | 1.98 | 2.09 | 1.87 |

The data show that the addition of sodium citrate to the RV medium prior to hybridization increases assay detection (O.D. at 450 nm) for *S. enteritidis*. The increase in O.D. for *S. typhimurium* was slight in the very low and high dilutions, but was noticeable in the mid-dilution range. This data is consistent with the fact that only certain Salmonella serovars exhibit the assay inhibition problem, and that various serovars exhibit different degrees of assay inhibition.

Other samples giving low GTS assay values with RV broth include the following: *S. ealing* in powdered baby milk, *S. manchester* in savory snacks, *S hadar* in raw chicken, *S. newport* in raw minced beef, and *S. enteritidis* in powdered egg (data not shown). In addition, tests for *S. enteritidis* in fresh eggs were performed using both the Gene-Trak GTS colorimetric assay following the manufacturer's instructions and conventional assays on selective plates using standard techniques.

For the Gene-Trak U.S. assay, the egg samples were preenriched in a standard preenrichment broth, aliquoted at 1.0 ml to 10.0 ml into either selenite cysteine or tetrathionate-brilliant green broths for enrichment, and then enriched further in GN broth at the same 1:10 ratio prior to assaying.

For the U.S. conventional assay, the same preenrichment and enrichment protocols were followed, except that the cultures were plated onto selective plates directly from the selenite or tetrathionate cultures rather than going through the final enrichment phase.

The European enrichment protocol utilized the same preenrichment step. Thereafter, 1.0 ml aliquots of the preenrichment broth are added to 10.0 ml of either RV medium or Mueller-Kauffman tetrathionate broth, and then plated onto selective plates for the conventional assay, or finally enriched in RV/GN medium prior to the GTS assay. These tests gave the following results.

| | RV Inhibition in Gene-Trak Assay | | | | |
| --- | --- | --- | --- | --- | --- |
| | | Gene-Trak Assay | | | |
| Organism | Inoculum | | | European | Conventional |
| CRA No. | (Cells/25 g) | US | MK | RV | US | European |
| 786 | 13 | + | + | +* | + | + |
| 787 | 12 | + | + | − | + | + |
| 788 | 23 | + | + | + | + | + |
| 789 | 19 | + | + | − | + | + |

(*= low value)

This table shows that the RV medium gives false negative readings for the GTS assay in 2 of the 4 assays and a false low value as 1 of the 2 positive readings.

Another test was conducted to show the elimination of RV medium assay inhibition using the method of the invention. Various *S. enteritidis* in fresh egg samples were cultured according to the U.S. and European protocols described above and assayed using the GTS assay. In addition, a protocol according to the invention was used, in which 0.1 ml of 0.6M sodium citrate was added to 0.5 ml RV medium to achieve a final concentration of 0.1M sodium citrate in the final enrichment phase.

As shown in the table below, the O.D. (450 nm) readings were comparable to the assays done in other growth media (standard U.S. and MK), whereas the RV medium without the addition of sodium citrate gave clearly false negatives. Furthermore, the column captioned "RV+CENT" shows that virtually comparable results can be obtained by centrifuging the sample, and resuspending the bacteria in fresh RV medium.

Removal of RV Inhibition in Gene-Trak Assay

| Organism CRA No. | Inoculum (Cells/25 g) | US | MK | European RV | RV + CENT | RV + CITRATE |
|---|---|---|---|---|---|---|
| 786 | 77 | 1.76 | 1.83 | 0.01 | 1.63 | 1.72 |
| 787 | 53 | 1.77 | 1.85 | 0.04 | 1.68 | 1.84 |
| 788 | 59 | 1.72 | 1.92 | 0.01 | 1.68 | 1.81 |
| 789 | 40 | 1.59 | 1.89 | 0.04 | 1.67 | 1.77 |

A number of experiments were also performed to compare the method of the invention, using sodium citrate in RV medium, to a number of different conventional enrichment protocols used in the U.S. and Europe. The U.S. and European enrichment protocols described above were used along with protocols using an RV plus sodium citrate medium according to the invention. Both GTS and conventional assays were used to test chicken, minced beef, fresh egg, powdered egg, powdered low fat milk, powdered baby milk, savory cheese snacks, chocolate, and reference samples (spray-dried milk in gelatine capsules).

Salmonella serotypes inoculated into food included *indiana, hadar, heidelberg, newport, agona, ibadan, enteritidis* PT4 (×6), *saint-paul, napoli, manchester* (×2), *infantis, ealing, virchow, arizona, typhimurium,* and *telel-kebir*.

The results of this study are shown in FIGS. 1A to 1D. All RV media samples pretreated with sodium citrate according to the invention gave virtually identical results to the other media samples, which, unlike untreated RV medium, do not interfere with the assays.

As shown in FIGS. 1A to 1D, and the table below, these studies show, for example, that there is no difference in sensitivity between using RV plus sodium citrate and MK medium for a wide range of Salmonella strains, where RV alone was shown to have many false negative reactions. The following table gives a summary of the evaluation of the GTS colorimetric assay for Salmonella incorporating the trace mineral removal method of the invention.

| | Gene Trak Assay | | | Conventional | |
|---|---|---|---|---|---|
| | | European | | | European |
| | USA | MK | RV + Na Citrate | USA | |
| TOTAL POSITIVES | 51 | 47 | 50 | 51 | 52 |
| FALSE NEGATIVES | 0 | 2 | 1 | — | — |

(Combinded European Total Positives = 51)
TOTAL POSITIVES BY ANY METHOD = 57

A number of tests were also conducted to determine the appropriate level of sodium citrate to achieve the desired enhancement of the hybridization signal. Results of these tests indicate that a final concentration within the range of 0.05 to 0.5M sodium citrate is suitable to enhance the hybridization signal. More preferably, the range is from about 0.1 to about 0.2M sodium citrate.

Other embodiments are within the following claims.

I claim:

1. A method for optimizing the hybridization signal of a nucleic acid hybridization assay for the DNA or RNA of Salmonella in a sample comprising adding the sample to RV medium under conditions sufficient to allow any Salmonella in said sample to propagate, propagating the Salmonella, if any, in said medium for a time sufficient to allow the number of Salmonella to reach a predetermined titer, removing trace minerals from said medium after said predetermined titer is reached, adding a nucleic acid probe to said medium under stringency conditions sufficient to allow said probe to hybridize with the DNA or RNA of Salmonella, if any, to form hybridization products, wherein said trace minerals are removed from said medium prior to hybridization and in an amount sufficient to prevent interference of the hybridization reaction, and assaying said medium to detect said hybridization products to provide an optimized hybridization signal.

2. The method of claim 1, wherein said trace mineral removal step comprises chelating said medium with an amount of a chelating agent sufficient to prevent interference of said hybridization of said probe with said DNA or RNA of Salmonella, if any, by said trace mineral in said medium.

3. The method of claim 2, wherein said trace mineral is magnesium.

4. The method of claim 2, wherein said chelating agent is sodium citrate.

5. The method of claim 2, wherein said chelating agent is ethylenediaminetetraacetic acid.

6. The method of claim 4, wherein said sodium citrate is added to said medium to achieve a final concentration of sodium citrate in said medium of 0.05M to 0.5M.

7. The method of claim 6, wherein said sodium citrate is added to said medium to achieve a final concentration of sodium citrate in said medium of 0.1M to 0.2M.

8. The method of claim 1, wherein the sample is a food product.

9. The method of claim 1, wherein said trace mineral removal step comprises centrifuging said RV medium to recover the Salmonella, if any, and resuspending the Salmonella in fresh RV medium.

10. A method for optimizing a nucleic acid hybridization assay for the DNA or RNA of Salmonella in a sample propagated in RV medium comprising adding the sample to RV medium under conditions sufficient to allow any Salmonella in the sample to propagate, propagating the Salmonella, if any, in said medium for a time sufficient to allow the number of Salmonella to reach a predetermined titer, adding a chelating agent to said medium after said predetermined titer is reached, and adding a nucleic acid probe to said medium under stringency conditions sufficient to allow said probe to hybridize with the DNA or RNA of Salmonella, if any, to form hybridization products, wherein said chelating agent is added prior to hybridization and in an amount sufficient to increase the hybridization reaction as compared to a hybridization reaction under the same conditions without an added chelating agent, thereby optimizing the nucleic acid hybridization assay.

\* \* \* \* \*

UNITED STATES PATENT AND TRADEMARK OFFICE
CERTIFICATE OF CORRECTION

PATENT NO. : 5,489,512

DATED : February 6, 1996

INVENTOR(S) : R. Scott McKenzie

It is certified that error appears in the above-identified patent and that said Letters Patent is hereby corrected as shown below:

On the title page, item [54], and Column 1,

In the Title:

Delete "MEDIA" and insert therefor --MEDIUM--.

In the Abstract:

Line 3, delete "a" (second occurrence).

Col. 1, line 24, delete "test" and insert therefor --tests--;

Col. 2, lines 62-67, delete entire paragraph;

Col. 3, line 2, delete "Tables" and insert therefor --Figures--;

Col. 3, line 4, delete "Tables" and insert therefor --Figures--;

Col. 3, line 49, delete "Gene-Trak Systems (GTS)", and insert therefor --GTS--;

UNITED STATES PATENT AND TRADEMARK OFFICE
CERTIFICATE OF CORRECTION

PATENT NO. : 5,489,512
DATED : February 6, 1996
INVENTOR(S) : R. Scott McKenzie

It is certified that error appears in the above-identified patent and that said Letters Patent is hereby corrected as shown below:

Col. 5, line 22, insert --US-- before "European" and above the column of numbers starting with "1.76";

Col. 5, line 24, delete "US";

Col. 5, line 62, insert --USA-- before "European" and above the columns including the number "51" (both occurrences); and Col. 5, line 64, delete "USA" (both occurrences).

Signed and Sealed this

Twenty-eighth Day of April, 1998

*Attest:*

BRUCE LEHMAN

*Attesting Officer*     *Commissioner of Patents and Trademarks*